United States Patent [19]
Hasebe et al.

[11] Patent Number: 5,622,911
[45] Date of Patent: Apr. 22, 1997

[54] METHOD FOR ENHANCING THE EFFICACY OF AGRICULTURAL CHEMICAL WITH ALKOXYLATED FATTY ACID AMIDES

[75] Inventors: Keiko Hasebe; Tadayuki Suzuki; Yuichi Hioki, all of Wakayama, Japan

[73] Assignee: Kao Corporation, Tokyo, Japan

[21] Appl. No.: 386,877

[22] Filed: Feb. 10, 1995

[30] Foreign Application Priority Data

Feb. 14, 1994 [JP] Japan .................................. 6-017454
Feb. 14, 1994 [JP] Japan .................................. 6-017455

[51] Int. Cl.$^6$ ................................................. A01N 25/30
[52] U.S. Cl. ........................ 504/116; 514/784; 514/785; 514/946; 554/63; 554/64
[58] Field of Search ........................... 504/116; 424/405; 514/784, 785, 946

[56] References Cited

FOREIGN PATENT DOCUMENTS

| | | |
|---|---|---|
| 56-135409 | 10/1981 | Japan . |
| 58-128301 | 7/1983 | Japan . |
| 58-118502 | 7/1983 | Japan . |
| 63-41884 | 8/1988 | Japan . |
| 1-301605 | 12/1989 | Japan . |
| 2-142708 | 5/1990 | Japan . |
| 2-295907 | 12/1990 | Japan . |
| 3-48602 | 3/1991 | Japan . |
| 4-41406 | 2/1992 | Japan . |
| 4-502618 | 5/1992 | Japan . |

OTHER PUBLICATIONS

Wyrill et al. "Glyphosote Toxicity . . . as Influenced by Surfactants". *Weed Science* 25(3):275–287. 1977.

*Primary Examiner*—S. Mark Clardy
*Attorney, Agent, or Firm*—Birch, Stewart, Kolasch & Birch

[57] ABSTRACT

The efficacy of an agricultural chemical can be enhanced by using a specific fatty acid alkanolamide or a fatty acid ester or carboxymethylated derivative thereof represented by the following formula (I) together with the agricultural chemical:

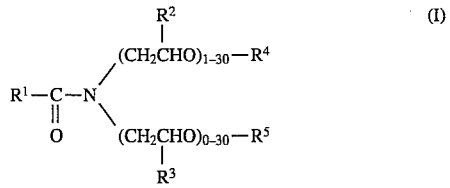

wherein $R^1$ represents a linear or branched alkyl or alkenyl group having 5 to 29 carbon atoms; each $R^2$ represents a hydrogen atom or a methyl group; each $R^3$ represents a hydrogen atom or a methyl group; $R^4$ and $R^5$ may be the same or different from each other and each independently represents a hydrogen atom, a group represented by the formula:

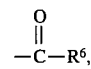

wherein $R^6$ represents a linear or branched alkyl or alkenyl group having 1 to 29 carbon atoms, or a group represented by the formula: —$CH_2COOX$, wherein X represents a hydrogen atom, a sodium atom, a potassium atom, an ammonium group or an organic ammonium group.

19 Claims, No Drawings

METHOD FOR ENHANCING THE EFFICACY OF AGRICULTURAL CHEMICAL WITH ALKOXYLATED FATTY ACID AMIDES

BACKGROUND OF THE INVENTION

1. Field of the Invention

The present invention relates to a method for enhancing the efficacy of an agricultural chemical, an enhancer for an agricultural chemical, an enhancer composition for an agricultural chemical, and an agricultural chemical composition.

2. Description of the Related Art

Agricultural chemicals including insecticides, fungicides (or bactericides), herbicides, miticides (or acaricides) and plant growth regulators have been used in the forms of, for example, emulsions, wettable powders, granules, dusts and flowables. In the properties of these agricultural chemical preparations, various attempts have been made to achieve the maximum effectiveness of the agricultural chemicals. However, it has been difficult to enhance the effectiveness of agricultural chemicals through adjustments in formulations. It is further difficult to develop novel agricultural chemicals. Therefore, further enhancement of existing agricultural chemicals would highly contribute to the industry.

As substances capable of enhancing the effectiveness of agricultural chemicals, surfactants comprising various nitrogen-containing compounds such as quaternary ammonium salts, betaines and amine oxides have been known. It is known that quaternized or further polyoxyethylenated long-chain amines, among the above-mentioned compounds, are effective for this purpose. However, the enhancement effect of the above described compounds capable of enhancing the effectiveness of agricultural chemicals is not always satisfied.

Fatty acid alkanolamides are known substances and have been used as a foam stabilizer for a shampoo or the like. Further, it has also been known to use fatty acid alkanolamides in the field of agricultural chemicals. However, they are used for stabilizing agricultural chemicals in many cases. In particular, Japanese Patent Publication-A No. 58-118502 (published on Jul. 14, 1983) discloses the use of an alkylolamide nonionic surfactant as an auxiliary for an alkali cyanate herbicide; Japanese Patent Publication-A No. 58-128301 (published on Jul. 30, 1983) discloses an aqueous agricultural chemical suspension comprising an agricultural chemical which is difficultly soluble or insoluble in water as an active ingredient, a polyhydric alcohol nonionic surfactant such as a fatty acid alkanolamide, a thickener and others; Japanese Patent Publication-A No. 1-301605 (published on Dec. 5, 1989) discloses a dust or wettable powder for agricultural and horticultural uses which comprises a specific silane compound as an active ingredient and a nonionic surfactant such as a fatty acid alkylolamide; Japanese Patent Publication-A No. 2-142708 (published on May 31, 1990) discloses a dust for indoor use which comprises a pyrethroid compound and/or an organophosphorus compound as an active ingredient, a fatty acid alkylolamide and others; Japanese Patent Publication-A No. 3-48602 (published on Mar. 1, 1991) discloses the addition of a fatty acid alkanolamide to a foaming agent used in the foam-spraying of a pest control agent; Japanese Patent Publication-A No. 4-41406 (published on Feb. 12, 1992) discloses the use or a fatty acid alkanolamide as a stabilizer for a pyrethroid insecticide; and Japanese Patent Publication-B No. 63-41884 (published on Aug. 19, 1988) discloses that a fatty acid alkanolamide exhibits effective insecticidal and/or ovicidal activity against epizoa.

DISCLOSURE OF THE INVENTION

Summary of the Invention

The present inventors have made studies for the purpose of finding a compound which can enhance the efficacy of an agricultural chemical. As a result of the studies, they have found that a specific fatty acid alkanolamide and a fatty acid ester thereof or a carboxymethylated derivative thereof can enhance the efficacies of various agricultural chemicals. Further, they have found that when such a fatty acid alkanolamide or a fatty acid ester or carboxymethylated derivative thereof is used together with a chelating agent, the efficacies of various agricultural chemicals can be enhanced more effectively. The present invention has been accomplished on the basis of these findings.

Thus, the present invention provides a method for enhancing the efficacy of an agricultural chemical which comprises applying at least one compound represented by the following formula (I) together with the agricultural chemical to a locus which would benefit from such treatment:

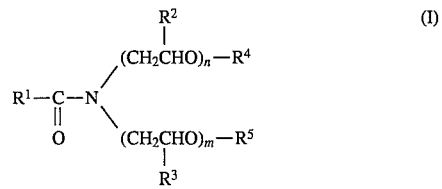

wherein $R^1$ represents a linear or branched alkyl or alkenyl group having 5 to 29 carbon atoms; each $R^2$ represents a hydrogen atom or a methyl group; each $R^3$ represents a hydrogen atom or a methyl group; $R^4$ and $R^5$ may be the same or different from each other and each independently represents a hydrogen atom, a group represented by the formula:

wherein $R^6$ represents a linear or branched alkyl or alkenyl group having 1 to 29 carbon atoms, or a group represented by the formula: —$CH_2COOX$, wherein X represents a hydrogen atom, a sodium atom, a potassium atom, an ammonium group or an organic ammonium group; m is a number of 0 to 30; and n is a number of 1 to 30.

According to the method of the present invention, the compound represented by the formula (I) and the agricultural chemical are generally diluted with water or a liquid medium prior to the application.

Examples of the locus or area to be treated include a farm, a plantation, a fruit garden, an orchard, a flower garden, a lawn, a wood and a forest. Examples of the locus or area to be treated also include plants, field crops such as cereals, vegetables and fruits, trees, fruit trees, grasses, weeds, seeds, and, at the same time, fungi, bacteria, insects, mites and acarids.

The letters m and n each represents the number of oxyalkylene groups, when a single compound is represented by the formula (I). In this case, m is 0 or an integer of 1 to 30 and n is an integer of 1 to 30.

Alternatively, m and n each represent the average number of oxyalkylene groups, when a mixture comprising compounds which are represented by the formula (I) and are different from one another only in the number of oxyalkylene groups is represented by the formula (I). In this case, m is a number of 0 to 30, and is a number of 1 to 30. In other words, the compound defined by the formula (I) includes a mixture of different compounds each having the formula (I) in view of the values of m and/or n. In this case, m and n each shows an average value of different m's and n's, respectively, and some of m's and n's may fall outside the range of 0 to 30 and 1 to 30, respectively.

The number of oxyalkylene groups per molecule is represented by the sum of m and n. When the compound represented by the formula (I) is one prepared through the addition reaction of an alkylene oxide with a fatty acid alkanolamide as will be described below, the number of alkylene oxide molecules added to each active hydrogen is m minus 1 or n minus 1.

The compound represented by the formula (I) includes compounds represented by the formula (I) wherein $R^4$ and $R^5$ are each a hydrogen atom, i.e., fatty acid alkanolamides represented by the following formula (I-A); ones represented by the formula (I) wherein $R^4$ and $R^5$ are each a group represented by the formula:

wherein $R^6$ is as defined above, or alternatively one of $R^4$ and $R^5$ is a group represented by the formula:

wherein $R^6$ is as defined above and the other is a hydrogen atom, i.e., fatty acid esters of fatty acid alkanolamides represented by the following formula (I-B); and ones represented by the formula (I) wherein $R^4$ and $R^5$ are each a group represented by the formula: —$CH_2COOX$, wherein X is as defined above, or alternatively one of $R^4$ and $R^5$ is a group represented by the formula: —$CH_2COOX$, wherein X is as defined above, and the other is a hydrogen atom, i.e., carboxymethylated derivatives of fatty acid alkanolamides represented by the following formula (I-C):

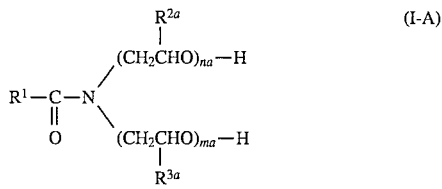

wherein $R^1$: represents a linear or branched alkyl or alkenyl group having 5 to 29 carbon atoms, $R^{2a}$, $R^{3a}$: represent the same or different from each other and, hydrogens or methyl groups or a mixture of a hydrogen(s) with a methyl group(s), na: represents a number of 1 to 30 on the average, and
ma: represents a number of 0 to 30 on the average;

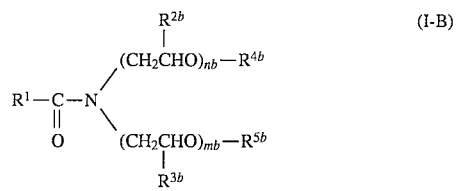

wherein $R^1$: represents a linear or branched alkyl or alkenyl group having 5 to 29 carbon atoms, $R^{2b}$, $R^{3b}$: represent the same or different from each other and, hydrogens or methyl groups or mixture of a hydrogen(s) with a methyl group(s), mb: represents a number of 0 to 30 on the average nb: represents a number of 1 to 30 on the average $R^{4b}$, $R^{5b}$: represent both

or a mixture of

with a hydrogen, and $R^6$: a linear or branched alkyl or alkenyl group having 1 to 29 carbon atoms;

and

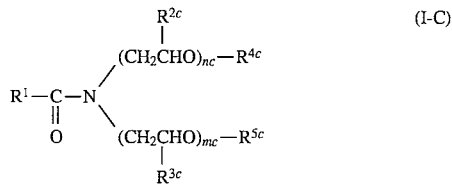

wherein $R^1$: represents a linear or branched alkyl or alkenyl group having 5 to 29 carbon atoms, $R^{2c}$, $R^{3c}$: represent the same or different from each other and, hydrogens or methyl groups or mixture of a hydrogen(s) with a methyl group(s), mc: represents a number of 0 to 30 on the average, nc: represents a number of 1 to 30 on the average, $R^{4c}$, $R^{5c}$: represent both —$CH_2COOXc$ or a mixture of —$CH_2COOXc$ with a hydrogen, and Xc: represents a hydrogen, Na, K, $NH_4$ or an organic ammonium cation.

Among compounds represented by the above formula (I-C), those represented by the formula (I-C) wherein $R^{4c}$ is a group represented by the formula: —$CH_2COOXc$, wherein Xc is as defined above, $R^{5c}$ is a hydrogen atom, and mc is 0 are preferred.

The present invention also provides an enhancer for an agricultural chemical comprising at least one compound represented by the above formula (I), and an enhancer composition for an agricultural chemical comprising at least one compound represented by the above formula (I) and a chelating agent wherein the amount of the chelating agent is 0.01 to 30 times by mole as large as the compound represented by the formula (I).

Further, the present invention provides an agricultural chemical composition comprising an agricultural chemical and at least one compound represented by the above formula (I) wherein the weight ratio of the compound represented by the formula (I) to the agricultural chemical ranges from 0.03 to 50.

The term "agricultural chemical" used in this specification refers to a substance used in a common agricultural chemical composition or agricultural chemical preparation as an active or principle ingredient, and examples thereof include a fungicide (a bactericide), an insecticide, a miticide (an acaricide), a herbicide, a plant growth regulator and the like.

Further scope and applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Detailed Description of the Invention

Among the compounds represented by the formula (I) according to the present invention, a compound represented by the formula (I) wherein $R^4$ and $R^5$ are each a hydrogen atom, i.e., a fatty acid alkanolamide can be prepared, e.g., as follows.

A fatty acid monoethanolamide can be prepared by reacting a fatty acid with monoethanolamine, and the resulting amide can further be conventionally converted into an adduct thereof with an alkylene oxide through the addition reaction of the alkylene oxide. Several adducts of fatty acid monoethanolamides with alkylene oxides are commercially available. For example, three adducts of coconut oil fatty acid monoethanolamide with ethylene oxide are commercially available under the trade names "Amizett 2C" (corresponding to a compound represented by the formula (I) wherein m is 0 and n is 2), "Amizett 5C" (corresponding to a compound represented, by the formula (I) wherein m is 0 and n is 5) and "Amizett 10C" (corresponding to a Compound represented by the formula (I) wherein m is 0 and n is 10) from Kawaken Fine Chemicals K.K.

A fatty acid dialkanolamide and an adduct thereof with alkylene oxide can be prepared in the same manner as that described above except that diethanolamine is used instead of the monoethanolamine. Further, another fatty acid alkanolamide represented by the formula (I) can be prepared in the same manner as that described above except that an isopropanolamine is used instead of the ethanolamine.

Among the compounds of the formula (I) according to the present invention, a fatty acid ester of fatty acid alkanolamide represented by the formula (I), wherein $R^4$ and $R^5$ are each a group represented by the formula:

wherein $R^6$ is as defined above or alternatively one of $R^4$ and $R^5$ is a group represented by the formula:

wherein $R^6$ is as defined above and the other is a hydrogen atom, can be prepared, e.g., as follows.

First, a fatty acid alkanolamide such as a fatty acid mono- or diethanolamide and an adduct thereof with alkylene oxide is prepared by the above process. Then, the obtained fatty acid alkanolamide is esterified with a fatty acid. Thus, a desired ester of fatty acid ethanolamide can be prepared.

Among the compounds of the formula (I) according to the present invention, a carboxylated derivative of fatty acid alkanolamide represented by the formula (I) wherein $R^4$ and $R^5$ are each a group represented by the formula: $-CH_2COOX$, wherein X is as defined above, or alternatively one of $R^4$ and $R^5$ is a group represented by the formula: $-CH_2COOX$, wherein X is as defined above, and the other is a hydrogen atom, i.e., a fatty acid amide (poly)oxyalkyleneacetate can be prepared by, e.g., a process which comprises reacting the above fatty acid alkanolamide with sodium monochloroacetate in the presence of an alkali, adding hydrochloric acid to the reaction product, and desalting the resulting mixture. Further, the fatty acid amide (poly)oxyalkyleneacetate thus prepared can be converted into a salt (corresponding to a compound represented by the formula (I) wherein X is not a hydrogen atom) thereof through neutralization with a basic compound corresponding to X, such as sodium hydroxide.

Of course, the process for preparing the compound of the formula (I) according to the present invention is not limited to those described above.

Among the compounds of the formula (I) according to the present invention, those represented by the formula (I) wherein m represents an average number and is a number of 0 to 20 and n represents an average number and is a number of 1 to 20 are desirable, and more desirable among them are those wherein m represents an average number and is a number of 0 to 10 and n represents an average number and is a number of 1 to 10. Among the compounds of the formula (I) according to the present invention, compounds represented by the formula (I) wherein m and n each represents an average number and lies in the above range and the sum of m and n is 1 or above but below 25 are most desirable.

Compounds represented by the formula (I) wherein $R^1$ is a linear or branched alkyl or alkenyl group having 7 to 21 carbon atoms are preferred, and those prepared by the use of coconut oil fatty acid, palm oil fatty acid, beef tallow fatty acid, lauric acid, myristic acid, palmitic acid, stearic acid or oleic acid as the starting fatty acid are still preferable.

It is preferable that all of $R^2$(s) and $R^3$(s) are each a hydrogen atom, i.e., that the oxyalkylene group(s) is(are) oxyethylene group(s), though at least one of $R^2$(s) and $R^3$(s) may represent a hydrogen atom(s) and other(s) may represent a methyl group(s), i.e., the (poly)oxyalkylene group(s) may be constituted with both oxyethylene group(s) and oxypropylene group(s). A compound represented by the formula (I) which contains oxyethylene group(s) and oxypropylene group(s) can be prepared by, e.g., reacting a fatty acid mono- or diethanolamide with propylene oxide through addition reaction or by reacting it with both ethylene oxide and propylene oxide through addition reaction. In the latter case, ethylene oxide and propylene oxide may be added at random, in block or alternately.

Among compound represented by the formula (I) wherein $R^4$ and/or $R^5$ is a group represented by the formula:

those represented by the formula (I) wherein $R^6$ is a linear or branched alkyl group having 1 to 21 carbon atoms or a linear or branched alkenyl group having 2 to 21 carbon atoms are preferable.

Further, among compounds of the formula (I) wherein $R^4$ and $R^5$ are each a group represented by the formula: —$CH_2COOX$, wherein X is as defined above, and compounds of the formula I) wherein one of $R^4$ and $R^5$ is a group represented by the formula: —$CH_2COOX$, wherein X is as defined above, and the other is a hydrogen atom, those represented by the formula (I) wherein $R^4$ is a group represented by the formula: —$CH_2COOX$, wherein X is as defined above, $R^5$ is a hydrogen atom and m is 0 are desirable. Among them, compounds represented by the formula (I) wherein n represents an average number and is a number of 1 to 20 are more desirable, and most desirable are those wherein n represents an average number and is a number of 1 to 10. In the formula, X is a hydrogen atom, a sodium atom, a potassium atom, an ammonium group or an organic ammonium group, and examples of the organic ammonium group include ammonium groups corresponding to primary, secondary and tertiary amines, such as a monoethanolammonium group, a diethanolammonium group, a triethanolammonium group, an isopropylammonium group and a diisopropylammonium group.

The enhancer for an agricultural chemical according to the present invention, i.e., the compound represented by the formula (I), can enhance the efficacy of an agricultural chemical by twice or thrice without causing any chemical injury to field crops when used together with the agricultural chemical.

Although the reasons why the enhancer for an agricultural chemical according to the present invention comprising the compound represented by the formula (I) exhibits a remarkable enhancing effect on an agricultural chemical independent of the structure of the chemical are not always apparent, one of them is believed to be that the enhancer of the present invention has a very high solubilizing effect on an agricultural chemical and therefore can improve the wettability of the agricultural chemical or can accelerate the penetration of the chemical into insects, fungi or bacteria.

When the compound represented by the formula (I) is used together with a chelating agent, the enhancing effect on an agricultural chemical can be further enhanced.

The chelating agent to be used in the present invention is not particularly limited, but may be any one having the ability to chelate a metal ion. Examples of the chelating agent to be used in the present invention include aminopolycarboxylic acid chelating agents, aromatic and aliphatic carboxylic acid chelating agents, amino acid chelating agents, ether polycarboxylic acid chelating agents, phosphonic acid chelating agents such as iminodimethylphosphonic acid (IDP) and an alkyldiphosphonic acid (ADPA), hydroxy carboxylic acid chelating agents, polyelectrolyte chelating agents (including oligoelectrolyte), and dimethylglyoxime (DG), which may each take a free acid form or a salt form such as a sodium salt, a potassium salt and an ammonium salt.

Specific examples of the aminopolycarboxylic acid chelating agent include:
a) compounds represented by the formula: $RNY_2$,
b) compounds represented by the formula: $NY_3$,
c) compounds represented by the formula: R—NY—$CH_2CH_2$—NY—R
d) compounds represented by the formula: R—NY—$CH_2CH_2$—$NY_2$
e) compounds represented by the formula: $Y_2N$—R'—$NY_2$, and
f) compounds which are similar to the compounds (e) and each has more than 4 Ys, for example, a compound represented by the formula:

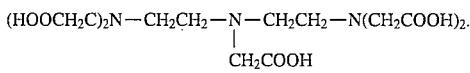

In the above formulae, Y represents —$CH_2COOH$ or —$CH_2CH_2COOH$; R represents any group constituting known chelating agents of this type, for example, a hydrogen atom, an alkyl group, a hydroxyl group or a hydroxyalkyl group; and R' represents any group constituting known chelating agents of this type, for example, an alkylene group or a cycloalkylene group.

Representative examples of the aminopolycarboxylic acid chelating agents include ethylenediaminetetraacetic acid (EDTA), cyclohexanediaminetetraacetic acid (CDTA), nitrilotriacetic acid (NTA), iminodiacetic acid (IDA), N-(2-hydroxyethyl)iminodiacetic acid (HIMDA), diethylenetriaminepentaacetic acid (DTPA), N-(2-hydroxyethyl)ethylenediaminetriacetic acid (EDTA-OH) and glycol ether diaminetetraacetic acid (GEDTA), and salts thereof.

Examples of the aromatic and alipatic carboxylic acid chelating agents to be used in the present invention include oxalic acid, pyruvic acid and anthranilic acid, and sales thereof. Further, examples of the amino acid chelating agents to be used in the present invention include glycine, serine, alanine, lysine, cystine, cysteine, ethionine, tyrosine and methionine, and salts and derivatives thereof.

Furthermore, examples of the ether polycarboxylic acid chelating agents to be used in the present invention include compounds represented by the following formula, analogues of them and salts thereof (such as sodium salts thereof):

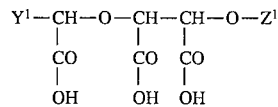

wherein $Y^1$ represents a hydrogen atom, —$CH_2COOH$ or —COOH; and $Z^1$ represents a hydrogen atom, —$CH_2COOH$ or

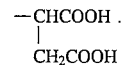

Examples of the hydroxy carboxylic acid chelating agents to be used in the present invention include malic acid, citric acid, glycolic acid, gluconic acid, heptonic acid and tartaric acid, and salts thereof.

Examples of the polyelectrolyte (including oligoelectrolyte) chelating agents to be used in the present invention include polyacrylic acid, polymaleic anhydride, α-hydroxyacrylic acid polymer, polyitaconic acid, copolymers comprising two or more of the monomers constituting these polymers, and epoxysuccinic acid polymer.

Among the above chelating agents, it is preferable to use an aromatic carboxylic acid chelating agent, an amine acid chelating agent, an ether polycarboxylic acid chelating agent, a phosphonic acid chelating agent, a polyelectrolyte (or oligoelectrolyte) chelating agent or dimethylglyoxime (DG).

According to the present invention, such a chelating agent is used in an amount of 0.01 to 30 mol, preferably 0.05 to 20 mol, still more preferably 0.1 to 15 mol per mole of the compound represented by the above formula (I) (per mole of the total amount when two or more compounds (I) are used).

It has been a practice in the prior art that a small amount of a chelating agent is added to a surfactant capable for enhancing the efficacy of an agricultural chemical [see Japanese Patent Publication-A Nos. 2-295907 (published on Dec. 6, 1990), 4-502618 (published on May 14, 1992) and 56-135409 (published on Oct. 22, 1981)]. However, the main purpose of the addition of a chelating agent according to the prior art is to trap inhibitors against an agricultural chemical i.e., trace metal ions (such as $Ca^{++}$ and $Mg^{++}$) contained in the water used in diluting the agricultural chemical to convert the hard water into soft water. Accordingly, the amount of the chelating agent added in the prior art is small, while in the present invention, a chelating agent is used in an increased amount as compared with that of the prior art.

The chelating agent thus used is believed to exhibit the effect of enhancing the efficacy of an agricultural chemical through some interaction with the compound represented by the formula (I). The effect of the chelating agent according to the present invention is thought to by essentially different from the above-mentioned effect of the prior art of trapping trace metal ions contained in water to thereby enhance the efficacy of an agricultural chemical. Actually, it was observed that the enhancing effect of the compound represented by the formula (I) according to the present invention on an agricultural chemical was enhanced by the addition of a chelating agent in distilled water as well as in hard water.

The amount of the compound represented by the formula (I) [hereinafter abbreviated to compound (I)] to be added can be reduced by using a surfactant other than the compounds (I) together with the compound (I) without lowering the enhancing effect of the compound (I) on an agricultural chemical.

Examples of the surfactant to be used together with the compound (I) include nonionic surfactants, anionic surfactants, cationic surfactants and amphoteric surfactants, and mixtures of two or more of them.

When the compound (I) is a fatty acid alkanolamide or a fatty acid ester thereof, the surfactant to be used therewith is preferably a nonionic surfactant, an anionic surfactant or a mixture of them, still more preferably a polyoxyalkylene alkylglycerol ester, while when the compound (I) is a carboxymethylated derivative of fatty acid alkanolamide, the surfactant to be used therewith is preferably a nonionic surfactant, a cationic surfactant, or a mixture of them.

According to the present invention, it is preferable that the weight ratio of the compound (I) to the surfactant other than the compounds (I) is from 1/10 to 50/1, still more preferably from 1/1 to 10/1.

The present invention also relates to an enhancer composition for an agricultural chemical which comprises a compound represented by the above formula (I), i.e., an enhancer for an agricultural chemical, and a chelating agent as described above and/or a surfactant as described above.

The compound (I) according to the present invention is used together with an agricultural chemical. The term "agricultural chemical" used in this specification refers to a compound used in a conventional agricultural chemical composition or agricultural chemical preparation as an active ingredient, for example, a fungicide (or a bactericide), an insecticide, a miticide (or an acaricide), a herbicide or a plant growth regulator.

According to the present invention, the weight ratio of the compound (I) to the agricultural chemical is generally from 0.03 to 50, preferably from 0.04 to 20, still more preferably from 0.1 to 10.

Examples of the herbicide include acid amide herbicides, urea herbicides, dipyridyl herbicides, diazine herbicides, S-triazine herbicides, nitrile herbicides, dinitroaniline herbicides, carbamate herbicides, diphenyl ether herbicides, phenol herbicides, benzoic acid herbicides, phenoxy herbicides, organophosphorus herbicides and aliphatic herbicides.

Among these herbicides, acid amide herbicides, diazine herbicides, nitrile herbicides, dinitroaniline herbicides, benzoic acid herbicides and organophosphorus herbicides are preferably used together with the compound (I). The use of an organophosphorus herbicide is still more preferable. Preferable specific examples of the organophosphorus herbicide include glyphosate [N-(phosphonomethyl)glycine] and salts thereof; bialaphos [sodium L-2-amino-4-[(hydroxy)(methyl)phosphinoyl]butyryl-L-alanyl-L-ananinate] and glyphosinate [ammonium DL-homoalanin-4-yl(methyl)phosphinate].

Examples of the plant growth regulator include MH (maleic hydrazide), ethephon [2-chloroethylphosphonic acid], UASTA and bialaphos.

The present invention also relates to an agricultural chemical composition comprising a compound represented by the formula (I), i.e., the enhancer for an agricultural chemical according to the present invention, and an agricultural chemical.

The agricultural chemical composition of the present invention may be formulated into a form selected from among a liquid preparation, an emulsion, a wettable powders, a granule, a powder, and a flowable and so forth, though the form of the composition is not limited. Accordingly, the agricultural chemical composition of the present invention may further contain, depending upon the formulation and form thereof, other additives such as a solvent, an emulsifying agent, a dispersing agent and a filler.

If necessary, the agricultural chemical composition of the present invention may further contain a chelating agent as described above, a surfactant other than the compounds (I), a pH regulator, an inorganic salt, and/or a thickener.

Further, the agricultural chemical composition of the present invention may contain one or more components selected from among a plant growth regulator other than those described above, a fertilizer and manure, a preservative, and so forth.

The agricultural chemical composition of the present invention may be formulated into one mixture or may take the form of a kit comprising two or more containers filled with the specific components respectively.

The agricultural chemical composition of the present invention is used to control fungi (or bacteria), insects, mites (or acarids) and herbage or to regulate the growth of plants.

The compound (I) according to the present invention is applied together with an agricultural chemical to a locus which would benefit from such treatment, i.e., the application of the compound (I) and the agricultural chemical. Generally, the compound (I) and the agricultural chemical are used together with water or a liquid medium. The useful process for applying the compound (I) according to the present invention includes (1) one which comprises applying an agricultural chemical composition containing the compound (I) and having a preparation form (if necessary, the agricultural chemical composition is diluted with, for example, tap water), (2) another one which comprises adding the compound (I) to an agricultural chemical composition which has been diluted with water, and (3) another one which comprises diluting the compound (I) with water to prepare a dilute solution, and diluting an agricultural chemical composition with the dilute solution thus obtained. The desired enhancement effect can be achieved by either means.

A desirable enhancing effect can be attained by any of these processes.

The agricultural chemical composition of the present invention includes a composition containing an agricultural chemical and the compound (I) in high concentrations and another composition containing them in concentrations suitable for use. When the former is used, the agricultural chemical composition is diluted with water, etc., for example, just before applying. On the other hand, the agricultural chemical compositions used in the above cases (2) and (3) include those containing the agricultural chemical in high concentration and being free from the compound (I).

The contents of an agricultural chemical and the compound (I) in the diluted solution are not limited. The desired content of the agricultural chemical in the diluted solution varies depending upon, for example, the kind of the agricultural chemical, the use thereof, and so forth, while the desired content of the compound (I) in the dilution varies depending upon, for example, the kind of the agricultural chemical to be mixed therewith.

The diluted liquid comprising an agricultural chemical and the compound (I) in proper amounts is applied to, for example, plants, crops, vegetables, fruits, trees, fruit trees, grasses, weeds or seeds, and, at the same time, to fungi, bacteria, insects, acarids or mites. In other words, the diluted liquid is applied to a farm, a plantation, a fruit garden, an orchard, a flower garden, a lawn, a wood and a forest.

EXAMPLES

The present invention will now be described in more detail by referring to the following Examples which should not be thought to limit the scope of the present invention.

Example 1

Various enhancer compositions for agricultural chemicals listed in Tables 4 to 7 were prepared by using compounds listed in Tables 1 to 3 and, if necessary, surfactants and chelating agents listed in Tables 4 to 7.

TABLE 1

| Compd. No. | Structure |
|---|---|
| (1) | $C_{11}H_{23}-\underset{\underset{O}{\|}}{C}-N\begin{array}{c}CH_2CH_2OH\\ CH_2CH_2OH\end{array}$ |
| (2) | $C_7H_{15}-\underset{\underset{O}{\|}}{C}-N\begin{array}{c}(CH_2CH_2O)_{12}H\\ (CH_2CH_2O)_{12}H\end{array}$ |
| (3) | $C_{11}H_{23}-\underset{\underset{O}{\|}}{C}-N\begin{array}{c}(CH_2CH_2O)_5H\\ (CH_2CH_2O)_5H\end{array}$ |
| (4) | $C_{13}H_{27}-\underset{\underset{O}{\|}}{C}-N\begin{array}{c}(CH_2CHO)_2-(CH_2CH_2O)_3H \text{ (CH}_3)\\ (CH_2CHO)_2-(CH_2CH_2O)_3H \text{ (CH}_3)\end{array}$ |

TABLE 1-continued

| Compd. No. | Structure |
|---|---|
| (5) | $C_{15}H_{31}-\underset{\underset{O}{\|}}{C}-N\begin{array}{c}(CH_2CH_2O)_5-(CH_2CHO)_2H \text{ (CH}_3)\\ (CH_2CH_2O)_5-(CH_2CHO)_2H \text{ (CH}_3)\end{array}$ |
| (6) | $C_{17}H_{33}-\underset{\underset{O}{\|}}{C}-N\begin{array}{c}(CH_2CH_2O)_5H\\ (CH_2CH_2O)_5H\end{array}$ |
| (7) | $C_{11}H_{23}-\underset{\underset{O}{\|}}{C}-\underset{\underset{H}{\|}}{N}-(CH_2CH_2O)_{10}H$ |
| (8) | $iso\text{-}C_{17}H_{35}-\underset{\underset{O}{\|}}{C}-\underset{\underset{H}{\|}}{N}-(CH_2CHO)_4-(CH_2CH_2O)_6H$ (CH$_3$) |
| (9) | $C_{17}H_{33}-\underset{\underset{O}{\|}}{C}-\underset{\underset{H}{\|}}{N}-(CH_2CH_2O)_{10}H$ |

TABLE 2

| Compd. No. | Structure |
|---|---|
| (10) | $C_7H_{15}-\underset{\underset{O}{\|}}{C}-\underset{\underset{H}{\|}}{N}-(CH_2CH_2O)_8-\underset{\underset{O}{\|}}{C}-C_{11}H_{23}$ |
| (11) | $C_{13}H_{27}-\underset{\underset{O}{\|}}{C}-\underset{\underset{H}{\|}}{N}-(CH_2CH_2O)_3-\underset{\underset{O}{\|}}{C}-C_7H_{15}$ |
| (12) | $iso\text{-}C_{17}H_{35}-\underset{\underset{O}{\|}}{C}-\underset{\underset{H}{\|}}{N}+CH_2CHO)+(CH_2CH_2O)_{10}-\underset{\underset{O}{\|}}{C}-CH_3$ (CH$_3$) |
| (13) | $C_{21}H_{43}-\underset{\underset{O}{\|}}{C}-\underset{\underset{H}{\|}}{N}-(CH_2CH_2O)_{15}-\underset{\underset{O}{\|}}{C}-C_5H_{11}$ |
| (14) | $C_{11}H_{23}-\underset{\underset{O}{\|}}{C}-N\begin{array}{c}(CH_2CH_2O)-\underset{\underset{O}{\|}}{C}-C_2H_5\\ (CH_2CH_2O)-\underset{\underset{O}{\|}}{C}-C_2H_5\end{array}$ |
| (15) | $C_{17}H_{33}-\underset{\underset{O}{\|}}{C}-N\begin{array}{c}(CH_2CH_2O)_8-\underset{\underset{O}{\|}}{C}-CH_3\\ (CH_2CH_2O)_8-H\end{array}$ |

TABLE 3

| Compd. No. | Structure |
|---|---|
| (16) | $C_7H_{15}-\underset{\underset{O}{\|}}{C}-N\begin{cases}(CH_2CH_2O)_{11}-\underset{\underset{}{\|}}{C}-C_{11}H_{23}\\(CH_2CH_2O)_{11}-\underset{\underset{O}{\|}}{C}-C_{11}H_{23}\end{cases}$ with C=O |
| (17) | $C_{13}H_{27}-\underset{\underset{O}{\|}}{C}-N\begin{cases}(CH_2CH_2O)_5-\underset{\underset{O}{\|}}{C}-C_{17}H_{35}\\(CH_2CH_2O)_5-H\end{cases}$ |
| (18) | $C_{21}H_{43}-\underset{\underset{O}{\|}}{C}-\underset{\underset{H}{\|}}{N}-(CH_2CH_2O)_{10}-CH_2COOH$ |
| (19) | $C_{11}H_{23}-\underset{\underset{O}{\|}}{C}-\underset{\underset{H}{\|}}{N}-(CH_2CH_2O)_4-CH_2COONa$ |
| (20) | $C_{17}H_{33}-\underset{\underset{O}{\|}}{C}-\underset{\underset{H}{\|}}{N}-(CH_2CH_2O)-CH_2COO^-\overset{+}{HN}(CH_2CH_2OH)_3$ |
| (21) | $C_7H_{15}-\underset{\underset{O}{\|}}{C}-\underset{\underset{H}{\|}}{N}-(CH_2CH_2O)_5-(CH_2\underset{\underset{CH_3}{\|}}{CH}O)_2-CH_2COONa$ |

TABLE 4

| Enhancer (compsn.) No. | Compd. No. (A) | Surfactant (B) and/or chelating agent (C) | (A)/-(B)/-(C) by wt. |
|---|---|---|---|
| 1 | (1) | — | 100/0/0 |
| 2 | (1) | POE(20) sorbitan monooleate | 80/0/20 |
| 3 | (1) | EDTA-4Na | 70/0/30 |
| 4 | (2) | — | 100/0/0 |
| 5 | (2) | POE(8) oleyl ether | 80/20/0 |
| 6 | (2) | POE(10) nonylphenyl ether | 80/20/0 |
| 7 | (3) | — | 100/0/0 |
| 8 | (3) | EDTA-4Na | 70/0/30 |
| 9 | (3) | POE(6) sorbitan monooleate | 80/20/0 |
| 10 | (4) | — | 100/0/0 |
| 11 | (4) | sodium POE(20) lauryl ether sulfate | 80/20/0 |
| 12 | (4) | POE(9) nonylphenyl ether | 80/20/0 |
| 13 | (5) | — | 100/0/0 |
| 14 | (5) | ETA-OH | 70/0/30 |
| 15 | (5) | sodium POE(10) lauryl ether acetate | 80/20/0 | note) POE is an abbreviation of polyoxyethylene and each figure in the parentheses means the average number of ethylene oxide molecules added (the same applies hereinafter).

TABLE 5

| Enhancer (compsn.) No. | Compd. No. (A) | Surfactant (B) and/or chelating agent (C) | (A)/-(B)/-(C) by wt. |
|---|---|---|---|
| 16 | (6) | — | 100/0/0 |
| 17 | (6) | triethanolamine POE(20) lauryl ether sulfate | 80/20/0 |
| 18 | (6) | POE(10) monooleate and NTA-3Na | 70/15/15 |
| 19 | (7) | — | 100/0/0 |
| 20 | (7) | POE(9) nonylphenyl ether | 80/20/0 |
| 21 | (7) | POE(4) oleyl ether | 80/20/0 |
| 22 | (8) | — | 100/0/0 |
| 23 | (8) | POE(20) lauryl ether | 80/20/0 |
| 24 | (8) | NTA-3Na | 80/0/20 |
| 25 | (9) | — | 100/0/0 |
| 26 | (9) | POE(6) sorbitan oleate | 80/20/0 |
| 27 | (9) | POE(8) oleyl ether and EDTA-4Na | 70/16/14 |
| 28 | POE(24) linear-alkyl(C94)amine | | — |
| 29 | trimethylmonostearylammonium chloride | | — |
| 30 | dimethyllaurylamine | | — | note) the enhancer Nos. 28 to 30 are comparative ones.

TABLE 6

| Enhancer (compsn.) No. | Compd. No. (A) | Surfactant (B) and/or chelating agent (C) | (A)/-(B)/-(C) by wt. |
|---|---|---|---|
| 31 | (10) | — | 100/0/0 |
| 32 | (10) | POE(20) sorbitan monooleate | 80/20/0 |
| 33 | (10) | CDTA-4Na | 80/0/20 |
| 34 | (11) | — | 100/0/0 |
| 35 | (11) | POE(6) sorbitan monooleate | 80/20/0 |
| 36 | (11) | POE(8) oleyl ether | 80/20/0 |
| 37 | (12) | — | 100/0/0 |
| 38 | (12) | sodium POE(20) lauryl ether sulfate | 85/15/0 |
| 39 | (12) | palm fatty acid ester of POE(18) glycerol | 80/20/0 |
| 40 | (13) | — | 100/0/0 |

TABLE 6-continued

| Enhancer (compsn.) No. | Compd. No. (A) | Surfactant (B) and/or chelating agent (C) | (A)/-(B)/-(C) by wt. |
|---|---|---|---|
| 41 | (13) | POE(7) sec.-alkyl($C_{12-13}$) ether | 85/15/0 |
| 42 | (13) | POE(20) sorbitan monolaurate | 80/20/0 |
| 43 | (14) | — | 100/0/0 |
| 44 | (14) | POE(8) oleyl ether | 85/15/0 |
| 45 | (14) | POE(8) oleyl ether and EDTA-4Na | 75/15/10 |
| 46 | (15) | — | 100/0/0 |
| 47 | (15) | POE(10) nonylphenyl ether | 85/15/0 |
| 48 | (15) | EDTA-4Na | 80/0/20 |
| 49 | (16) | — | 100/0/0 |
| 50 | (16) | palm fatty acid ester of POE(18) glycerol | 85/15/0 |
| 51 | (16) | palm fatty acid ester of POE(18) glycerol and ETA-OH | 70/20/10 |

TABLE 7

| Enhancer (compsn.) No. | Compd. No. (A) | Surfactant (B) and/or chelating agent (C) | (A)/-(B)/-(C) by wt. |
|---|---|---|---|
| 52 | (17) | — | 100/0/0 |
| 53 | (17) | polyethylene glycol(10) monooleate | 85/15/0 |
| 54 | (17) | triethanolamine lauryl POE(10) ether sulfate | 85/15/0 |
| 55 | (18) | — | 100/0/0 |
| 56 | (18) | POE(10) laurylamine | 85/15/0 |
| 57 | (18) | POE(15) laurylamine and methionine | 70/15/15 |
| 58 | (19) | — | 100/0/0 |
| 59 | (19) | POE(15) beef tallow amine | 80/20/0 |
| 60 | (19) | POE(10) nonylphenyl ether and NTA-3Na | 70/20/10 |
| 61 | (20) | — | 100/0/0 |
| 62 | (20) | cysteine | 90/0/10 |
| 63 | (20) | palm fatty acid ester of POE(18) glycerol | 85/15/0 |
| 64 | (21) | — | 100/0/0 |
| 65 | (21) | POE(20) stearylamine | 80/20/0 |
| 66 | (21) | POE(10) nonylphenyl ether | 85/15/0 |
| 67 | POE(24) linear alkyl($C_{22}$)amine | | — |
| 68 | trimethylmonooctylammonium chloride | | — |
| 69 | trimethylmonododecylammonium chloride | | — | note) the enhancer Nos. 67 to 69 are comparative ones.

The chemical formulae of the chelating agents listed in the Tables 4 to 7 are as follows:

EDTA-4Na

NaOOCCH$_2$_____CH$_2$COONa
              NCH$_2$CH$_2$N
NaOOCCH$_2$/            \CH$_2$COONa

NTA-3Na

CH$_2$COONa
              /
NaOOCCH$_2$N
              \
                CH$_2$COONa

ETA-OH

CH$_2$COONa
|
CHCOONa
|
O
|
CHCOONa
|
CHCOONa
|
OH

CDTA-4Na

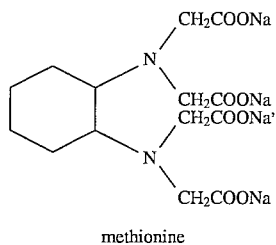

methionine

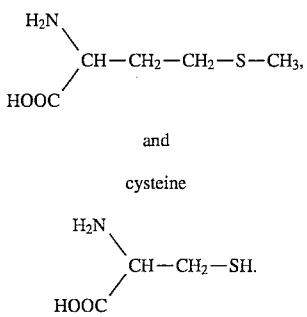

and cysteine

H$_2$N\
      CH—CH$_2$—SH.
HOOC/

The enhancers (or enhancer compositions) listed in the Tables 4 to 7 were each dissolved in deionized water to give dilutions having a concentration of 0.2% by weight. Commercially available herbicides, i.e., Roundup liquid formulation (containing 41% by weight of isopropylamine salt of glyphosate as the active ingredient), Banvel D liquid formulation (containing 50% by weight of dimethylamine salt of MDBA as the active ingredient) and Herbiace water-soluble powder (containing 20% by weight of bialaphos as the active ingredient) were each diluted 300-fold with each of the 0.2% by weight dilutions prepared above. Thus, three kinds of agricultural chemical composition were prepared from each enhancer (composition).

Fertile soil from a paddy field, gravel (i.e., river sand) and a commercially available compost were mixed together at a weight ratio of 7:2:1. The obtained mixture was put in pots each having an inner diameter of 12 cm. In order to conduct a greenhouse test, seeds of crabgrass were planted in the pots and germitated. The pots wherein the growth of crabgrass was abnormal were excluded in order to lower the non-uniformity among the pots. When the height of crabgrass reached about 18 cm, the resulting pots were used in the following test. The crabgrass of each pot was homogeneously sprayed with each of the above agricultural chemical compositions by the use of a spray gum (mfd. by Iwata Air Compressor Mfg. Co., Ltd., RG type) in a dose of 1000 l/ha (liter/hecto are) to evaluate the herbicidal efficacy of the agricultural chemical composition.

Ten days after the spraying, the above-ground part of the fresh plant was weighed and the result was expressed in a herbicidal ratio on the basis of the fresh weight of the above-ground part in the untreated lot (see the following formula).

$$\text{Herbicidal ratio (\%)} = \frac{\begin{array}{c}\text{above-ground} \\ \text{fresh weight} \\ \text{(g) of an} \\ \text{untreated lot}\end{array} - \begin{array}{c}\text{above-ground} \\ \text{fresh weight} \\ \text{(g) of a} \\ \text{test lot}\end{array}}{\text{above-ground fresh weight}} \times 100$$
$$\text{(g) of an untreated lot}$$

The herbicidal ratios of the agricultural chemical compositions are given in Tables 8 to 11.

TABLE 8

| | Enhancer (compsn.) No. | Banvel D liq. formulation | Herbiace water-sol. powder | Roundup liq. formulation |
|---|---|---|---|---|
| | | Herbicidal ratio (%) | | |
| Invention product | 1 | 83.4 | 89.0 | 94.5 |
| | 2 | 81.5 | 88.4 | 93.0 |
| | 3 | 84.0 | 89.6 | 95.8 |
| | 4 | 85.0 | 92.0 | 96.0 |
| | 5 | 84.0 | 90.4 | 94.4 |
| | 6 | 83.5 | 90.0 | 93.8 |
| | 7 | 89.0 | 94.8 | 97.8 |
| | 8 | 91.5 | 94.0 | 98.0 |
| | 9 | 87.5 | 92.8 | 95.7 |
| | 10 | 84.6 | 92.4 | 96.0 |
| | 11 | 84.0 | 91.4 | 95.0 |
| | 12 | 82.0 | 90.0 | 94.4 |
| | 13 | 86.2 | 93.0 | 97.5 |
| | 14 | 87.0 | 94.2 | 97.0 |
| | 15 | 84.1 | 93.0 | 96.4 |

TABLE 9

| | Enhancer (compsn.) No. | Banvel D liq. formulation | Herbiace water-sol. powder | Roundup liq. formulation |
|---|---|---|---|---|
| | | Herbicidal ratio (%) | | |
| Invention product | 16 | 90.4 | 95.0 | 98.0 |
| | 17 | 88.5 | 94.0 | 96.8 |
| | 18 | 90.2 | 95.4 | 98.0 |
| | 19 | 86.2 | 90.6 | 94.0 |
| | 20 | 84.8 | 88.2 | 92.0 |
| | 21 | 85.0 | 89.1 | 92.0 |
| | 22 | 84.0 | 89.8 | 93.5 |
| | 23 | 82.0 | 87.5 | 92.0 |
| | 24 | 85.2 | 90.4 | 93.0 |
| | 25 | 89.0 | 95.0 | 96.0 |
| | 26 | 85.0 | 92.0 | 94.2 |
| | 27 | 94.2 | 96.4 | 96.8 |
| Comp. product | 28 | 70.2 | 73.4 | 76.8 |
| | 29 | 68.8 | 70.6 | 72.1 |
| | 30 | 64.6 | 64.8 | 69.4 |
| not added | | 58.1 | 64.0 | 68.4 |

TABLE 10

| | Enhancer (compsn.) No. | Banvel D liq. formulation | Herbiace water-sol. powder | Roundup liq. formulation |
|---|---|---|---|---|
| | | Herbicidal ratio (%) | | |
| Invention product | 31 | 82.4 | 89.0 | 94.7 |
| | 32 | 80.3 | 88.0 | 92.4 |
| | 33 | 82.4 | 86.4 | 96.1 |
| | 34 | 84.4 | 92.4 | 95.8 |
| | 35 | 82.2 | 92.0 | 94.0 |
| | 36 | 84.0 | 92.0 | 96.2 |
| | 37 | 74.6 | 90.8 | 92.6 |
| | 38 | 72.4 | 90.0 | 92.0 |
| | 39 | 78.0 | 94.4 | 96.2 |

TABLE 10-continued

| Enhancer (compsn.) No. | Banvel D liq. formulation | Herbiace water-sol. powder | Roundup liq. formulation |
|---|---|---|---|
| | Herbicidal ratio (%) | | |
| 40 | 78.0 | 91.0 | 93.0 |
| 41 | 74.5 | 86.2 | 89.0 |
| 42 | 76.0 | 88.6 | 90.4 |
| 43 | 85.2 | 95.4 | 96.2 |
| 44 | 80.6 | 94.0 | 95.0 |
| 45 | 85.0 | 96.0 | 98.8 |
| 46 | 79.2 | 94.2 | 95.0 |
| 47 | 76.4 | 90.4 | 92.0 |
| 48 | 78.0 | 92.0 | 96.0 |
| 49 | 86.4 | 96.4 | 97.0 |
| 50 | 87.0 | 95.8 | 97.0 |

TABLE 11

| | Enhancer (compsn.) No. | Banvel D liq. formulation | Herbiace water-sol. powder | Roundup liq. formulation |
|---|---|---|---|---|
| | | Herbicidal ratio (%) | | |
| Invention product | 51 | 90.4 | 98.0 | 99.4 |
| | 52 | 81.6 | 88.5 | 90.4 |
| | 53 | 75.0 | 85.0 | 88.6 |
| | 54 | 78.4 | 90.4 | 91.2 |
| | 55 | 78.5 | 85.6 | 89.4 |
| | 56 | 76.2 | 86.0 | 93.0 |
| | 57 | 81.3 | 90.4 | 95.2 |
| | 58 | 88.5 | 95.0 | 98.0 |
| | 59 | 90.4 | 97.4 | 99.6 |
| | 60 | 93.6 | 98.2 | 99.8 |
| | 61 | 82.4 | 88.0 | 94.2 |
| | 62 | 80.2 | 86.2 | 95.0 |
| | 63 | 83.4 | 88.4 | 94.2 |
| | 64 | 80.5 | 90.4 | 95.0 |
| | 65 | 82.4 | 92.2 | 96.4 |
| | 66 | 78.6 | 88.6 | 93.2 |
| Comp. product | 67 | 62.4 | 68.2 | 75.1 |
| | 68 | 58.0 | 64.0 | 68.2 |
| | 69 | 60.2 | 65.0 | 72.3 |
| not added | | 55.3 | 62.0 | 65.3 |

Example 2

Female imagines of *Tetranychus kanzawai kishida* were planted onto kidney bean leaf disks at a ratio of 30 imagines per lot on three runs and then incubated at 25° C. for 24 hours. Then, the whole of a leaf disk was dipped in a test solution for 5 seconds. After taking out of the test solution and allowing to stand at 25° C. for 48 hours, the leaf disk was observed and the miticidal ratio thereof was determined on the basis of the result in the untreated lot (refer to the following equation).

$$\text{Miticidal ratio (\%)} = \frac{\begin{array}{c}\text{the number of} \\ \text{living mites of} \\ \text{an untreated lot}\end{array} - \begin{array}{c}\text{the number of} \\ \text{living mites} \\ \text{of a test lot}\end{array}}{\text{the number of living mites of an untreated lot}} \times 100$$

Nissolan wettable powder (containing 10% by weight of hexythiazox as the active ingredient) and Osadan wettable powder 25 (containing 25% by weight of fenbutatin oxide as the active ingredient), as miticides, were each diluted 2000-fold (with the use of deionized water as the diluent) and the resulting dilutions were each used. The same enhancers (or enhancer compositions) as those used in the Example 1 were used. The concentration of each enhancer (composition) for agricultural chemicals in the test solution was 0.1% by weight. Further, the same procedure as that described above was repeated except that no enhancer (composition) was used. The results are given in Tables 12 to 15.

TABLE 12

|  | Enhancer (compsn.) No. | Miticidal ratio (%) | |
|---|---|---|---|
|  |  | Nissolan wettable powder | Osadan wettable powder 25 |
| Invention product | 1 | 92.2 | 93.3 |
|  | 2 | 88.9 | 92.2 |
|  | 3 | 92.2 | 95.6 |
|  | 4 | 95.6 | 93.3 |
|  | 5 | 93.3 | 88.9 |
|  | 6 | 91.1 | 90.0 |
|  | 7 | 100 | 100 |
|  | 8 | 100 | 98.9 |
|  | 9 | 97.8 | 94.4 |
|  | 10 | 95.6 | 94.4 |
|  | 11 | 92.2 | 90.0 |
|  | 12 | 93.3 | 93.3 |
|  | 13 | 94.4 | 98.9 |
|  | 14 | 100 | 100 |
|  | 15 | 96.7 | 97.8 |

TABLE 13

|  | Enhancer (compsn.) No. | Miticidal ratio (%) | |
|---|---|---|---|
|  |  | Nissolan wettable powder | Osadan wettable powder 25 |
| Invention product | 16 | 92.2 | 95.6 |
|  | 17 | 94.4 | 92.2 |
|  | 18 | 94.4 | 90.0 |
|  | 19 | 98.9 | 97.8 |
|  | 20 | 92.2 | 93.3 |
|  | 21 | 91.1 | 91.1 |
|  | 22 | 88.9 | 83.3 |
|  | 23 | 87.8 | 77.8 |
|  | 24 | 93.3 | 83.3 |
|  | 25 | 95.6 | 96.7 |
|  | 26 | 92.2 | 93.3 |
|  | 27 | 97.8 | 97.8 |
| Comp. product | 28 | 66.7 | 65.6 |
|  | 29 | 55.6 | 56.7 |
|  | 30 | 47.7 | 50.0 |
| not added |  | 45.6 | 44.4 |

TABLE 14

|  | Enhancer (compsn.) No. | Miticidal ratio (%) | |
|---|---|---|---|
|  |  | Nissolan wettable powder | Osadan wettable powder 25 |
| Invention product | 31 | 86.7 | 88.9 |
|  | 32 | 84.4 | 88.9 |
|  | 33 | 86.7 | 92.2 |
|  | 34 | 88.9 | 93.3 |
|  | 35 | 84.4 | 91.1 |
|  | 36 | 84.4 | 88.9 |
|  | 37 | 91.1 | 94.4 |
|  | 38 | 88.9 | 92.2 |
|  | 39 | 91.1 | 88.9 |
|  | 40 | 88.9 | 92.2 |
|  | 41 | 86.7 | 91.1 |

TABLE 14-continued

| Enhancer (compsn.) No. | Miticidal ratio (%) | |
|---|---|---|
|  | Nissolan wettable powder | Osadan wettable powder 25 |
| 42 | 90.0 | 92.2 |
| 43 | 96.7 | 98.9 |
| 44 | 96.7 | 96.7 |
| 45 | 96.7 | 98.9 |
| 46 | 94.4 | 96.7 |
| 47 | 92.2 | 95.6 |
| 48 | 92.2 | 93.3 |
| 49 | 96.7 | 98.9 |
| 50 | 93.3 | 95.6 |
| 51 | 97.8 | 100 |

TABLE 15

|  | Enhancer (compsn.) No. | Miticidal ratio (%) | |
|---|---|---|---|
|  |  | Nissolan wettable powder | Osadan wettable powder 25 |
| Invention product | 52 | 83.3 | 88.9 |
|  | 53 | 82.2 | 87.8 |
|  | 54 | 82.2 | 86.7 |
|  | 55 | 93.3 | 90.0 |
|  | 56 | 94.4 | 93.3 |
|  | 57 | 96.7 | 98.9 |
|  | 58 | 98.9 | 100 |
|  | 59 | 96.7 | 100 |
|  | 60 | 100 | 100 |
|  | 61 | 88.9 | 90.0 |
|  | 62 | 82.2 | 87.8 |
|  | 63 | 86.7 | 86.7 |
|  | 64 | 90.0 | 93.3 |
|  | 65 | 93.3 | 94.4 |
|  | 66 | 90.0 | 92.2 |
| Comp. product | 67 | 64.4 | 64.4 |
|  | 68 | 48.9 | 52.2 |
|  | 69 | 50.8 | 54.4 |
| not added |  | 44.4 | 46.7 |

Example 3

The whole of a leaf disk of green bean was dipped in a test solution for 5 seconds. After taking out of the test solution and air-drying, ten leafhopper larvae of third instar preliminarily incubated were put on the leaf disk. After incubating at 25° C. for 10 days, the number of dead leafhoppers was determined with the naked eye to calculate the insecticidal ratio. This test was effected thrice in total, and the insecticidal ratio was determined in the same manner as the one employed for the determination of the miticidal ratio. Commercially available insecticides, i.e., Dimilin wettable powder (containing 23.5% by weight of difulubenzuron as the active ingredient) and Applaud wettable powder (containing 25.0% by weight of buprofezin as the active ingredient) were each diluted 2000-fold (with the use of deionized water as the diluent) and the obtained dilutions were each used. As the enhancers (and enhancer compositions) for agricultural chemicals, those employed in Example 1 were used in such a manner as to adjust the concentration of each enhancer (composition) in the diluted solution to 0.1% by weight.

The results are given in Tables 16 and 17.

TABLE 16

| | Enhancer (compsn.) No. | Insecticidal ratio (%) | |
|---|---|---|---|
| | | Dimilin wettable powder | Applaud wettable powder |
| Invention product | 1 | 90.0 | 93.3 |
| | 2 | 83.3 | 90.0 |
| | 3 | 86.7 | 93.3 |
| | 4 | 93.3 | 96.7 |
| | 5 | 90.0 | 90.0 |
| | 6 | 86.7 | 93.3 |
| | 7 | 100 | 100 |
| | 8 | 93.3 | 100 |
| | 9 | 90.0 | 96.7 |
| | 10 | 90.0 | 93.3 |
| | 11 | 86.7 | 86.7 |
| | 12 | 86.7 | 90.0 |
| | 13 | 93.3 | 96.7 |
| | 14 | 90.0 | 100 |
| | 15 | 86.7 | 93.3 |

TABLE 17

| | Enhancer (compsn.) No. | Insecticidal ratio (%) | |
|---|---|---|---|
| | | Dimilin wettable powder | Applaud wettable powder |
| Invention product | 16 | 90.0 | 100 |
| | 17 | 83.3 | 100 |
| | 18 | 86.7 | 96.7 |
| | 19 | 93.3 | 96.7 |
| | 20 | 86.7 | 93.3 |
| | 21 | 90.0 | 93.3 |
| | 22 | 86.7 | 90.0 |
| | 23 | 83.3 | 86.7 |
| | 24 | 80.0 | 93.3 |
| | 25 | 90.0 | 93.3 |
| | 26 | 83.3 | 86.7 |
| | 27 | 93.3 | 90.0 |
| Comp. product | 28 | 66.7 | 63.3 |
| | 29 | 60.0 | 56.7 |
| | 30 | 56.7 | 53.3 |
| not added | | 56.7 | 46.7 |

Example 4

(1) Leafhopper larvae of third instar were incubated and used in the test for evaluating the efficacy of an insecticide according to the three-run dipping method (wherein ten larvae were used in each lot). The insecticidal ratio was determined in the same manner as the one employed for the determination of the miticidal ratio. Commercially available insecticides, i.e., Sumithion emulsifiable concentrate (containing 50% by weight of MEP as the active ingredient) and Agrothrin wettable powder (containing 6% by weight of cypermethrin as the active ingredient) were each diluted 2000-fold (with the use of deionized water as the diluent) and the obtained dilutions were used. As the enhancers (and enhancer compositions) for agricultural chemicals, those employed in Example 1 were used in such a manner as to adjust the concentration of each enhancer (composition) in the diluted solution to 0.1% by weight.

(2) The same procedure as that of Example 3 was repeated except that Dimilin wettable powder was used as the insecticide to determine the insecticidal ratio.

The results are given in Tables 18 and 19.

TABLE 18

| | Enhancer (compsn.) No. | Insecticidal ratio (%) | | |
|---|---|---|---|---|
| | | Sumithion emulsifiable concentrate | Agrothrin emulsifiable concentrate | Dimilin wettable powder |
| Invention product | 31 | 86.7 | 80.0 | 86.7 |
| | 32 | 83.3 | 83.3 | 83.3 |
| | 33 | 83.3 | 80.0 | 83.3 |
| | 34 | 86.7 | 83.3 | 86.7 |
| | 35 | 80.0 | 83.3 | 83.3 |
| | 36 | 86.7 | 86.7 | 86.7 |
| | 37 | 90.0 | 86.7 | 90.0 |
| | 38 | 86.7 | 90.0 | 86.7 |
| | 39 | 86.7 | 86.7 | 86.7 |
| | 40 | 83.3 | 80.0 | 86.7 |
| | 41 | 80.0 | 80.0 | 83.3 |
| | 42 | 86.7 | 83.3 | 83.3 |
| | 43 | 96.7 | 93.3 | 96.7 |
| | 44 | 93.3 | 90.0 | 93.3 |
| | 45 | 90.0 | 90.0 | 93.3 |
| | 46 | 93.3 | 96.7 | 96.7 |
| | 47 | 90.0 | 96.7 | 96.7 |
| | 48 | 86.7 | 93.3 | 96.7 |
| | 49 | 86.7 | 86.7 | 90.0 |
| | 50 | 90.0 | 86.7 | 90.0 |
| | 51 | 93.3 | 93.3 | 96.7 |

TABLE 19

| | Enhancer (compsn.) No. | Insecticidal ratio (%) | | |
|---|---|---|---|---|
| | | Sumithion emulsifiable concentrate | Agrothrin emulsifiable concentrate | Dimilin wettable powder |
| Invention product | 52 | 90.0 | 86.7 | 86.7 |
| | 53 | 86.7 | 86.7 | 83.3 |
| | 54 | 90.0 | 83.3 | 83.3 |
| | 55 | 93.3 | 90.0 | 93.3 |
| | 56 | 93.3 | 96.7 | 96.7 |
| | 57 | 100 | 96.7 | 100.0 |
| | 58 | 96.7 | 93.3 | 96.7 |
| | 59 | 96.7 | 90.0 | 96.7 |
| | 60 | 100 | 96.7 | 100.0 |
| | 61 | 90.0 | 90.0 | 93.3 |
| | 62 | 86.7 | 90.0 | 86.7 |
| | 63 | 86.7 | 90.0 | 90.0 |
| | 64 | 96.7 | 90.0 | 90.0 |
| | 65 | 93.3 | 86.7 | 93.3 |
| | 66 | 93.3 | 86.7 | 90.0 |
| Comp. product | 67 | 56.7 | 60.0 | 60.0 |
| | 68 | 50.0 | 53.3 | 56.7 |
| | 69 | 46.7 | 53.3 | 56.7 |
| not added | | 46.7 | 50.0 | 53.3 |

Example 5

A spore suspension ($10^7$/ml) of cucumber *Botrytis cinerea* acquiring the resistance against fungicides was applied to young cucumber seedlings at the trifoliate stage in a dose of 10 ml per pot and the resulting seedlings were allowed to stand at 25° C. under a relative humidity of 90% for one day.

Then, a commercially available fungicide, i.e., Benlate wettable powder (Containing 50% by weight of benomyl as the active ingredient) was diluted 2000-fold with a 2500-fold dilution (wherein deionized water was used as the diluent) of each enhancer (composition) used in the Example 1. The dilutions thus prepared were each applied to the seedlings in a dose of 5 ml per pot. After allowing the pots to stand at 25° C. under a relative humidity of 85%, lesions were counted and the preventive value was calculated in accordance with the following equation.

The results are given in Tables 20 to 23.

$$\text{preventive value} = \left[1 - \frac{\text{no. of lesions of a test lot}}{\text{no. of lesion of an untreated lot}}\right] \times 100$$

TABLE 20

|  | Enhancer (compsn.) No. | Preventive value Benlate wettable powder |
|---|---|---|
| Invention product | 1 | 86 |
|  | 2 | 80 |
|  | 3 | 88 |
|  | 4 | 88 |
|  | 5 | 78 |
|  | 6 | 80 |
|  | 7 | 100 |
|  | 8 | 100 |
|  | 9 | 94 |
|  | 10 | 86 |
|  | 11 | 80 |
|  | 12 | 80 |
|  | 13 | 88 |
|  | 14 | 94 |
|  | 15 | 86 |

TABLE 21

|  | Enhancer (compsn.) No. | Preventive value Benlate wettable powder |
|---|---|---|
| Invention product | 16 | 100 |
|  | 17 | 94 |
|  | 18 | 98 |
|  | 19 | 94 |
|  | 20 | 90 |
|  | 21 | 88 |
|  | 22 | 88 |
|  | 23 | 84 |
|  | 24 | 88 |
|  | 25 | 94 |
|  | 26 | 90 |
|  | 27 | 96 |
| Comp. product | 28 | 74 |
|  | 29 | 72 |
|  | 30 | 60 |
| not added |  | 60 |

TABLE 22

|  | Enhancer (compsn.) No. | Preventive value Benlate wettable powder |
|---|---|---|
| Invention product | 31 | 84 |
|  | 32 | 82 |
|  | 33 | 82 |
|  | 34 | 86 |
|  | 35 | 80 |
|  | 36 | 86 |
|  | 37 | 88 |
|  | 38 | 91 |
|  | 39 | 90 |
|  | 40 | 92 |
|  | 41 | 90 |
|  | 42 | 88 |
|  | 43 | 95 |
|  | 44 | 92 |
|  | 45 | 92 |
|  | 46 | 96 |
|  | 47 | 92 |
|  | 48 | 90 |

TABLE 22-continued

|  | Enhancer (compsn.) No. | Preventive value Benlate wettable powder |
|---|---|---|
|  | 49 | 88 |
|  | 50 | 90 |
|  | 51 | 96 |

TABLE 23

|  | Enhancer (compsn.) No. | Preventive value Benlate wettable powder |
|---|---|---|
| Invention product | 52 | 90 |
|  | 53 | 88 |
|  | 54 | 88 |
|  | 55 | 96 |
|  | 56 | 98 |
|  | 57 | 100 |
|  | 58 | 96 |
|  | 59 | 100 |
|  | 60 | 100 |
|  | 61 | 92 |
|  | 62 | 90 |
|  | 63 | 90 |
|  | 64 | 86 |
|  | 65 | 82 |
|  | 66 | 86 |
| Comp. product | 67 | 60 |
|  | 68 | 64 |
|  | 69 | 68 |
| not added |  | 58 |

The above Examples 1 to 5 show tests whereby the efficacies of the enhancers (and enhancer compositions) for agricultural chemicals of the present invention were compared with those of common tertiary amine compounds and cationic surfactants (comparative products) employed as enhancers for agricultural chemicals.

As Tables 8 to 23 clearly show, the enhancers (and enhancer compositions) for agricultural chemicals according to the present invention exhibited remarkable effects of enhancing the efficacy of the agricultural chemicals, and were practically usable. On the contrary, the comparative products could slightly enhance the efficacies of the agricultural chemicals, but the enhancing effect was not enough for practical use. Accordingly, it can be understood that the enhancers (and enhancer compositions) for agricultural chemicals according to the present invention specifically enhance the efficacies of the agricultural chemicals as compared with the common tertiary amine compounds and cationic surfactants.

Example 6

The same test as that of the Example 1 was conducted by using Roundup liquid formulation (containing 41% by weight of an active ingredient) as a herbicide and the enhancers (and enhancer compositions) Nos. 7, 18, 25, 43, 51 and 58 used in Example 1 each in the amount specified in Tables 24 and 45.

The results are given in the Tables 24 and 25.

In the Tables, "Herbicide concn." means the concentration of the commercially available herbicide preparation in the dilution to be applied; "Enhancer (composition) concn." means the concentration of each enhancer (composition) in the dilution to be applied; and "Agricultural chemical"

means the active ingredient as the agricultural chemical contained in each herbicide preparation.

TABLE 24

| Test No. | Enhancer (compsn.) No. | Herbicide concn. (ppm) | Enhancer (compsn.) concn. (ppm) | Agricultural chemical/ enhancer (compsn.) by wt. | Herbicidal ratio (%) |
|---|---|---|---|---|---|
| 1 | No. 7 | 2000 | 50 | 1/0.06 | 85.0 |
| 2 | | 2000 | 100 | 1/0.12 | 88.5 |
| 3 | | 2000 | 500 | 1/0.6 | 91.3 |
| 4 | | 2000 | 1000 | 1/1.2 | 92.4 |
| 5 | | 2000 | 5000 | 1/6 | 96.8 |
| 6 | | 2000 | 10000 | 1/12 | 96.0 |
| 7 | | 2000 | 30000 | 1/37 | 95.9 |
| 8 | No. 18 | 2000 | 50 | 1/0.06 | 88.1 |
| 9 | | 2000 | 100 | 1/0.12 | 90.0 |
| 10 | | 2000 | 500 | 1/0.6 | 91.5 |
| 11 | | 2000 | 1000 | 1/1.2 | 93.0 |
| 12 | | 2000 | 5000 | 1/6 | 95.0 |
| 13 | | 2000 | 10000 | 1/12 | 96.2 |
| 14 | | 2000 | 30000 | 1/37 | 95.0 |
| 15 | No. 25 | 2000 | 50 | 1/0.06 | 82.4 |
| 16 | | 2000 | 100 | 1/0.12 | 85.2 |
| 17 | | 2000 | 500 | 1/0.6 | 88.8 |
| 18 | | 2000 | 1000 | 1/1.2 | 91.0 |
| 19 | | 2000 | 5000 | 1/6 | 96.4 |
| 20 | | 2000 | 10000 | 1/12 | 96.0 |
| 21 | | 2000 | 30000 | 1/37 | 94.5 |
| 22 | — | 2000 | 0 | — | 60.5 |

TABLE 25

| Test No. | Enhancer (compsn.) No. | Herbicide concn. (ppm) | Enhancer (compsn.) concn. (ppm) | Agricultural chemical/ enhancer (compsn.) by wt. | Herbicidal ratio (%) |
|---|---|---|---|---|---|
| 23 | No. 43 | 2000 | 50 | 1/0.06 | 80.8 |
| 24 | | 2000 | 100 | 1/0.12 | 86.2 |
| 25 | | 2000 | 500 | 1/0.6 | 89.4 |
| 26 | | 2000 | 1000 | 1/1.2 | 93.6 |
| 27 | | 2000 | 5000 | 1/6 | 93.6 |
| 28 | | 2000 | 10000 | 1/12 | 92.0 |
| 29 | | 2000 | 30000 | 1/37 | 92.0 |
| 30 | No. 51 | 2000 | 50 | 1/0.06 | 86.4 |
| 31 | | 2000 | 100 | 1/0.12 | 90.6 |
| 32 | | 2000 | 500 | 1/0.6 | 92.2 |
| 33 | | 2000 | 1000 | 1/1.2 | 95.0 |
| 34 | | 2000 | 5000 | 1/6 | 96.5 |
| 35 | | 2000 | 10000 | 1/12 | 93.0 |
| 36 | No. 58 | 2000 | 30000 | 1/37 | 90.0 |
| 37 | | 2000 | 50 | 1/0.06 | 84.2 |
| 38 | | 2000 | 100 | 1/0.12 | 90.6 |
| 39 | | 2000 | 500 | 1/0.6 | 93.4 |
| 40 | | 2000 | 1000 | 1/1.2 | 96.0 |
| 41 | | 2000 | 5000 | 1/6 | 97.4 |
| 42 | | 2000 | 10000 | 1/12 | 93.8 |
| 43 | | 2000 | 30000 | 1/37 | 92.0 |
| 44 | — | 2000 | 0 | — | 58.6 |

Example 7

The same test as that of the Example 3 was conducted by using Applaud wettable powder (containing 25.0% by weight of buprofezin as the active ingredient) as an insecticide and the enhancers Nos. 1 and 19 used in Example 1 each in the amount as specified in Table 26.

The results are given in the Table 26.

In the Table, "Insecticide concn." means the concentration of the commercially available insecticide preparation in the dilution to be applied; "Enhancer concn." means the concentration of each enhancer in the dilution to be applied; and "Agricultural chemical" means the active ingredient as the agricultural chemical contained in the insecticide preparation.

TABLE 26

| Test No. | Enhancer No. | Insecticide concn. (ppm) | Enhancer concn. (ppm) | Agricultural chemical/enhancer by wt. | Insecticidal ratio (%) |
|---|---|---|---|---|---|
| 1 | No. 1 | 500 | 10 | 1/0.04 | 86.7 |
| 2 | | 500 | 25 | 1/0.1 | 86.7 |
| 3 | | 500 | 250 | 1/1 | 93.3 |
| 4 | | 500 | 1000 | 1/4 | 93.3 |
| 5 | | 500 | 2500 | 1/10 | 96.7 |
| 6 | | 500 | 5000 | 1/20 | 93.3 |
| 7 | No. 19 | 500 | 10 | 1/0.04 | 86.7 |
| 8 | | 500 | 25 | 1/0.1 | 90.0 |
| 9 | | 500 | 250 | 1/1 | 93.3 |
| 10 | | 500 | 1000 | 1/4 | 96.7 |
| 11 | | 500 | 2500 | 1/10 | 96.7 |
| 12 | | 500 | 5000 | 1/20 | 93.3 |
| 13 | — | 500 | — | — | 46.7 |

Example 8

The same test as that of the Example 4(1) was conducted by using Sumithion emulsifiable concentrate (containing 50% by weight of MEP as the active ingredient) as an insecticide and the enhancer (and enhancer composition) Nos. 43 and 60 used in Example 1 each in the amount specified in Table 27.

The results are given in the Table 27.

In the Table, "Insecticide concn." means the concentration of the commercially available insecticide preparation in, the dilution to be applied; "Enhancer (composition) concn." means the concentration of each enhancer (composition) in the dilution to be applied; and "Agricultural chemical" means the active ingredient as the agricultural chemical contained in the insecticide preparation.

TABLE 27

| Test No. | Enhancer No. | Insecticide concn. (ppm) | Enhancer concn. (ppm) | Agricultural chemical/enhancer by wt. | Insecticidal ratio (%) |
|---|---|---|---|---|---|
| 1 | No. 43 | 250 | 10 | 1/0.08 | 80.0 |
| 2 | | 250 | 25 | 1/0.2 | 86.7 |
| 3 | | 250 | 250 | 1/2 | 90.0 |
| 4 | | 250 | 1000 | 1/8 | 93.3 |
| 5 | | 250 | 2500 | 1/20 | 93.3 |
| 6 | | 250 | 5000 | 1/40 | 90.0 |
| 7 | No. 60 | 250 | 10 | 1/0.08 | 83.3 |
| 8 | | 250 | 25 | 1/0.2 | 90.0 |
| 9 | | 250 | 250 | 1/2 | 93.3 |
| 10 | | 250 | 1000 | 1/8 | 96.7 |
| 11 | | 250 | 2500 | 1/20 | 96.7 |
| 12 | | 250 | 5000 | 1/40 | 93.3 |
| 13 | — | 250 | — | — | 50.0 |

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for enhancing the efficacy of an agricultural chemical which comprises applying at least one compound represented by the following formula (I) together with the agricultural chemical to a locus which would benefit from such treatment:

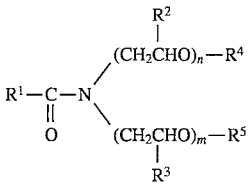

(I)

wherein $R^1$ represents a linear or branched alkyl or alkenyl group having 5 to 29 carbon atoms; each $R^2$ represents a hydrogen atom or a methyl group; each $R^3$ represents a hydrogen atom or a methyl group; $R^4$ and $R^5$ may be the same or different from each other and each independently represents a hydrogen atom, a group represented by the formula:

wherein $R^6$ represents a linear or branched alkyl or alkenyl group having 1 to 29 carbon atoms, or a group represented by the formula: $-CH_2COOX$, wherein $R^4$ and $R^5$ are not both hydrogen, wherein X represents a hydrogen atom, a sodium atom, a potassium atom, an ammonium group or an organic ammonium group; m is a number of 0 to 30; and n is a number of 1 to 30.

2. The method for enhancing the efficacy of an agricultural chemical as set forth in claim 1, wherein the $R^4$ and $R^5$ in the formula (I) are each a group represented by the formula:

or alternatively one of them is a group represented by the formula:

and the other is a hydrogen atom.

3. The method for enhancing the efficacy of an agricultural chemical as set forth in claim 1, wherein the $R^4$ and $R^5$ in the formula (I) are each a group represented by the formula: —$CH_2COOX$, or alternatively one of them is a group represented by the formula: —$CH_2COOX$, and the other is a hydrogen atom.

4. The method for enhancing the efficacy of an agricultural chemical as set forth in claim 3, wherein $R^4$ is a group represented by the formula: —$CH_2COOX$, $R^5$ is a hydrogen atom; and m is 0.

5. The method for enhancing the efficacy of an agricultural chemical as set forth in claim 4, wherein the at least one compound of formula (I) is:

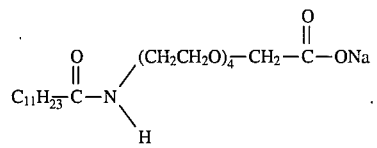

6. The method for enhancing the efficacy of an agricultural chemical as set forth in claim 1, wherein m is an average number of from 0 to 20, n is an average number of from 1 to 20, and the sum of m and n is a number of 1 or above but below 25.

7. The method for enhancing the efficacy of an agricultural chemical as set forth in claim 1, wherein the agricultural chemical is a fungicide, insecticide, miticide, herbicide or plant growth regulator.

8. The method for enhancing the efficacy of an agricultural chemical as set forth in claim 7, wherein the agricultural chemical is a herbicide.

9. The method for enhancing the efficacy of an agricultural chemical as set forth in claim 7, wherein the agricultural chemical is an organophosphorus herbicide.

10. The method for enhancing the efficacy of an agricultural chemical as set forth in claim 1, wherein the weight ratio of the compound of formula (I) to the agricultural chemical is 0.03 to 50.

11. The method for enhancing the efficacy of an agricultural chemical as set forth in claim 1, further adding a chelating agent in an amount 0.01 to 30 times by mole as large as the compound of formula (I).

12. The method for enhancing the efficacy of an agricultural chemical as set forth in claim 1, further adding a surfactant other than the compounds represented by the formula (I) at a weight ratio of the compound of formula (I) to the surfactant of 1/10 to 50/1.

13. An enhancer composition for an agricultural chemical comprising at least one compound represented by the following formula (I) and a chelating agent, wherein the amount of the chelating agent is 0.01 to 30 times by mole as large as the compound represented by the formula (I):

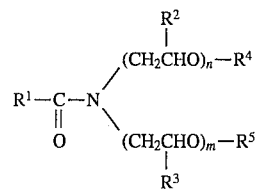

wherein $R^1$ represents a linear or branched alkyl or alkenyl group having 5 to 29 carbon atoms; each $R^2$ represents a hydrogen atom or a methyl group; each $R^3$ represents a hydrogen atom or a methyl group; $R^4$ and $R^5$ may be the same or different from each other and each independently represents a hydrogen atom, a group represented by the formula:

wherein $R^6$ represents a linear or branched alkyl or alkenyl group having 1 to 29 carbon atoms, or a group represented by the formula: —$CH_2COOX$, wherein $R^4$ and $R^5$ are not both hydrogen, wherein X represents a hydrogen atom, a sodium atom, a potassium atom, an ammonium group or an organic ammonium group; m is a number of 0 to 30; and n is a number of 1 to 30.

14. The enhancer composition for an agricultural chemical as set forth in claim 13, which further comprises a surfactant other than the compounds represented by the formula (I) at a weight ratio of the compound represented by the formula (I) to the surfactant of 1/10 to 50/1.

15. The enhancer composition for an agricultural chemical as set forth in claim 13 wherein said at least one compound represented by formula (I) is:

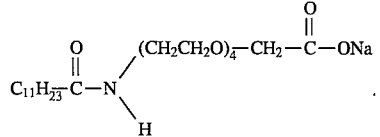

16. An agricultural chemical composition comprising an agricultural chemical and at least one compound represented by the following formula (I), wherein the weight ratio of the compound represented by the following formula (I) to the agricultural chemical ranges from 0.03 to 50:

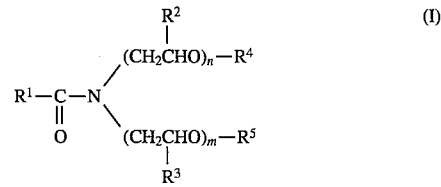

wherein $R^1$ represents a linear or branched alkyl or alkenyl group having 5 to 29 carbon atoms; each $R^2$ represents a hydrogen atom or a methyl group; each $R^3$ represents a hydrogen atom or a methyl group; $R^4$ and $R^5$ may be the same or different from each other and each independently represents a hydrogen atom, a group represented by the formula:

wherein $R^6$ represents a linear or branched alkyl or alkenyl group having 1 to 29 carbon atoms, or a group represented by the formula: —$CH_2COOX$, wherein $R^4$ and $R^5$ are not both hydrogen wherein X represents a hydrogen atom, a sodium atom, a potassium atom, an ammonium group or an organic ammonium group; m is a number of 0 to 30; and n is a number of 1 to 30.

17. The agricultural chemical composition as set forth in claim 16, which further comprises a chelating agent in an amount 0.01 to 30 times by mole as large as the compound represented by the formula (I).

18. The agricultural chemical composition as set forth in claim 16, which further comprises a surfactant other than the compounds represented by the formula (I) at a weight ratio of the compound represented by the formula (I) to the surfactant of 1/10 to 50/1.

19. The agricultural chemical composition as set forth in claim 16, wherein said at least one compound represented by formula (I) is:

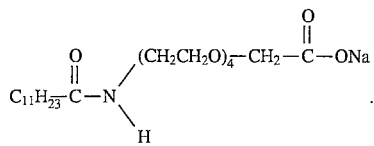

* * * * *